United States Patent
Govari et al.

(10) Patent No.: US 9,675,411 B2
(45) Date of Patent: Jun. 13, 2017

(54) CATHETER WITH PERFORATED TIP

(75) Inventors: Assaf Govari, Haifa (IL); Athanassios Papaioannou, Los Angeles, CA (US); Andres Claudio Altman, Haifa (IL)

(73) Assignee: Biosense Webster, Inc., Diamond Bar, CA (US)

(*) Notice: Subject to any disclaimer, the term of this patent is extended or adjusted under 35 U.S.C. 154(b) by 953 days.

(21) Appl. No.: 12/173,150

(22) Filed: Jul. 15, 2008

(65) Prior Publication Data
US 2010/0030209 A1    Feb. 4, 2010

(51) Int. Cl.
*A61B 18/14* (2006.01)
*A61B 18/18* (2006.01)
*A61B 18/00* (2006.01)
*A61N 7/02* (2006.01)

(52) U.S. Cl.
CPC ...... *A61B 18/1492* (2013.01); *A61B 18/1477* (2013.01); *A61B 18/18* (2013.01); *A61B 2018/00577* (2013.01); *A61B 2018/1425* (2013.01); *A61B 2218/002* (2013.01); *A61N 7/022* (2013.01); *Y10T 29/49826* (2015.01)

(58) Field of Classification Search
CPC . A61B 18/14; A61B 18/1402; A61B 18/1477; A61B 18/148; A61B 18/1482; A61B 18/1485; A61B 18/1487; A61B 2018/1405; A61B 2018/1417; A61B 2018/1472
USPC ......... 606/22–28, 32, 34, 41, 20, 21, 47–50; 607/101–102
See application file for complete search history.

(56) References Cited

U.S. PATENT DOCUMENTS

| | | | | |
|---|---|---|---|---|
| 4,770,171 A | * | 9/1988 | Sweren et al. | 606/25 |
| 5,391,199 A | | 2/1995 | Ben-Haim | |
| 5,419,767 A | * | 5/1995 | Eggers et al. | 604/114 |
| 5,462,521 A | * | 10/1995 | Brucker et al. | 604/20 |
| 5,545,161 A | | 8/1996 | Imran | |
| 5,582,609 A | * | 12/1996 | Swanson et al. | 606/39 |
| 5,688,267 A | | 11/1997 | Panescu et al. | |
| 5,735,846 A | | 4/1998 | Panescu et al. | |
| 5,800,428 A | * | 9/1998 | Nelson et al. | 606/41 |
| 5,800,432 A | * | 9/1998 | Swanson | 606/49 |
| 5,904,651 A | | 5/1999 | Swanson et al. | |
| 5,947,988 A | * | 9/1999 | Smith | 606/167 |

(Continued)

FOREIGN PATENT DOCUMENTS

| | | |
|---|---|---|
| EP | 0 956 826 B1 | 11/1999 |
| EP | 0 982 047 A2 | 3/2000 |

(Continued)

OTHER PUBLICATIONS

Partial EP Search Report EP 09 25 1788 dated Sep. 24, 2009.

(Continued)

*Primary Examiner* — Michael Peffley
*Assistant Examiner* — Khadijeh Vahdat

(57) ABSTRACT

A medical device includes an insertion tube, having a distal end for insertion into a body of a subject. A distal tip is fixed to the distal end of the insertion tube and is coupled to apply energy to tissue inside the body. The distal tip has an outer surface with a plurality of perforations through the outer surface, which are distributed circumferentially and longitudinally over the distal tip. A lumen passes through the insertion tube and is coupled to deliver a fluid to the tissue via the perforations.

15 Claims, 3 Drawing Sheets

(56) References Cited

U.S. PATENT DOCUMENTS

| | | | |
|---|---|---|---|
| 5,964,757 A | 10/1999 | Ponzi | |
| 6,110,196 A * | 8/2000 | Edwards | 607/96 |
| 6,129,698 A | 10/2000 | Beck | |
| 6,210,411 B1 | 4/2001 | Hofmann | |
| 6,217,576 B1 * | 4/2001 | Tu et al. | 606/41 |
| 6,458,123 B1 * | 10/2002 | Brucker et al. | 606/41 |
| 6,464,694 B1 * | 10/2002 | Massengill | 606/15 |
| 6,576,858 B1 * | 6/2003 | Yokomichi | 219/69.2 |
| 6,690,963 B2 | 2/2004 | Ben-Haim et al. | |
| 7,104,989 B2 * | 9/2006 | Skarda | 606/41 |
| 7,258,689 B2 | 8/2007 | Salvo | |
| 7,549,989 B2 * | 6/2009 | Morgan et al. | 606/41 |
| 7,815,635 B2 | 10/2010 | Wittkampf et al. | |
| 7,901,403 B2 * | 3/2011 | Woloszko et al. | 606/48 |
| 8,224,422 B2 | 7/2012 | Mottola et al. | |
| 8,500,730 B2 | 8/2013 | Lee et al. | |
| 2001/0025179 A1 | 9/2001 | Levine | |
| 2001/0051802 A1 * | 12/2001 | Woloszko et al. | 606/41 |
| 2003/0009094 A1 | 1/2003 | Segner et al. | |
| 2003/0163178 A1 * | 8/2003 | Davison et al. | 607/101 |
| 2003/0212394 A1 | 11/2003 | Pearson et al. | |
| 2004/0243157 A1 * | 12/2004 | Connor et al. | 606/159 |
| 2005/0085769 A1 * | 4/2005 | MacMahon et al. | 604/96.01 |
| 2006/0184165 A1 * | 8/2006 | Webster et al. | 606/41 |
| 2006/0241577 A1 * | 10/2006 | Balbierz et al. | 606/32 |
| 2006/0264808 A1 * | 11/2006 | Staid et al. | 604/22 |
| 2007/0270791 A1 | 11/2007 | Wang et al. | |
| 2007/0287998 A1 | 12/2007 | Sharareh et al. | |
| 2008/0161792 A1 | 7/2008 | Wang et al. | |
| 2008/0255540 A1 | 10/2008 | Selkee | |
| 2008/0287944 A1 | 11/2008 | Pearson et al. | |
| 2009/0093810 A1 * | 4/2009 | Subramaniam et al. | 606/41 |
| 2009/0125016 A1 | 5/2009 | Wang et al. | |
| 2009/0209949 A1 | 8/2009 | Ingle et al. | |
| 2010/0030209 A1 | 2/2010 | Govari et al. | |
| 2010/0069834 A1 | 3/2010 | Schultz | |
| 2010/0168827 A1 | 7/2010 | Schultz | |
| 2011/0264089 A1 | 10/2011 | Zirkle et al. | |
| 2011/0270244 A1 | 11/2011 | Clark | |
| 2011/0270246 A1 | 11/2011 | Clark | |

FOREIGN PATENT DOCUMENTS

| | | |
|---|---|---|
| EP | 1690510 A | 8/2006 |
| EP | 1 803 410 A1 | 7/2007 |
| EP | 2145596 A | 1/2010 |
| EP | 2380519 A | 10/2011 |
| JP | 2009-148550 A | 7/2009 |
| JP | 2010-505592 A | 2/2010 |
| WO | WO 02/083228 A2 | 10/2002 |
| WO | WO 2011/008681 A | 1/2011 |

OTHER PUBLICATIONS

State Intellectual Property Office of People's Republic of China Search Report dated Jul. 30, 2012.
European Search Report dated Aug. 4, 2011 in related European Application No. 11163515.7.
European Search Report dated May 26, 2014 in related European Application No. 14158294.0.
Japanese Notification of Reasons for Refusal dated Nov. 11, 2014 in related Japanese Application No. 2011-096838.
Related U.S. Appl. No. 12/767,763 filed Apr. 26, 2010.

* cited by examiner

CATHETER WITH PERFORATED TIP

FIELD OF THE INVENTION

The present invention relates generally to medical devices, and specifically to cooling of tissue contacted by an invasive probe within the body.

BACKGROUND OF THE INVENTION

In some medical procedures, energy is imparted to body tissue locally, in a concentrated dose, and it is desirable to cool the treatment area in order to reduce collateral tissue damage.

For example, cardiac ablation therapy is used to treat arrhythmias by heating tissue with radio-frequency (RF) electrical energy to create non-conducting lesions in the myocardium. It has been found that cooling the area of the ablation site reduces tissue charring and thrombus formation. For this purpose, Biosense Webster Inc. (Diamond Bar, Calif.) offers the ThermoCool® irrigated-tip catheter as part of its integrated ablation system. The metal catheter tip, which is energized with RF current to ablate the tissue, has a number of peripheral holes, distributed circumferentially around the tip, for irrigation of the treatment site. A pump coupled to the catheter delivers saline solution to the catheter tip, and the solution flows out through the holes during the procedure in order to cool the catheter tip and the tissue.

SUMMARY OF THE INVENTION

Despite the general usefulness of irrigation in reducing collateral tissue damage, the inventors have found that in some cases, the tissue and treatment device in the vicinity of the treatment area are not adequately or uniformly cooled. Problems may arise, for example, due to blockage of the irrigation holes in the treatment catheter.

Embodiments of the present invention that are described hereinbelow provide multiple perforations in the distal tip of a treatment device, such as a catheter or other probe. The perforations are distributed both circumferentially and longitudinally over the distal tip. The large number of perforations and their longitudinal distribution help to ensure adequate irrigation of the entire distal tip and treatment area and thus reduce collateral tissue damage, as well as preventing adhesion of the distal tip to the tissue.

There is therefore provided, in accordance with an embodiment of the present invention, a medical device, including:

an insertion tube, having a distal end for insertion into a body of a subject;

a distal tip, which is fixed to the distal end of the insertion tube and is coupled to apply energy to tissue inside the body, and which has an outer surface with a plurality of perforations through the outer surface, which are distributed circumferentially and longitudinally over the distal tip; and a lumen passing through the insertion tube and coupled to deliver a fluid to the tissue via the perforations.

Typically, the plurality of the perforations includes at least eight perforations and may include at least fifty perforations. In a disclosed embodiment, the perforations have a diameter less than 0.5 mm, and may have a diameter less than 0.2 mm. Additionally or alternatively, the perforations may have respective sizes that vary depending on respective longitudinal locations of the perforations.

There is also provided, in accordance with an embodiment of the present invention, medical apparatus, including:

an elongate probe, for insertion into a body of a subject, the probe including:

an insertion tube, having a distal end for insertion into the body;

a distal tip, which is fixed to the distal end of the insertion tube and is coupled to apply energy to tissue inside the body, and which has an outer surface with a plurality of perforations through the outer surface, which are distributed circumferentially and longitudinally over the distal tip; and a lumen passing through the insertion tube and in fluid communication with the perforations;

an energy generator, for coupling to the probe so as to supply the energy to the distal tip; and an irrigation pump, for coupling to the lumen so as to supply a fluid via the lumen and the perforations to the tissue.

In a disclosed embodiment, the outer surface of the distal tip includes a conductive material and is configured to contact the tissue, and the energy generator is coupled to supply electrical energy to the distal tip in order to ablate the tissue. In one embodiment, the elongate probe is configured for insertion through a blood vessel into a heart of the subject for ablation of myocardial tissue in the heart.

There is additionally provided, in accordance with an embodiment of the present invention, a method for treatment, including:

inserting an elongate probe into a body of a subject, the probe including:

an insertion tube, having a distal end for insertion into the body;

a distal tip, which is fixed to the distal end of the insertion tube and which has an outer surface with a plurality of perforations through the outer surface, which are distributed circumferentially and longitudinally over the distal tip; and a lumen passing through the insertion tube and in fluid communication with the perforations;

applying energy through the distal tip to tissue inside the body; and supplying a fluid via the lumen and the perforations to the tissue.

Typically, supplying the fluid includes cooling the distal tip and the tissue.

There is further provided, in accordance with an embodiment of the present invention, a method for producing a medical device, including:

creating a plurality of perforations through an outer surface of a distal tip of the medical device, such that the perforations are distributed circumferentially and longitudinally over the distal tip;

fixing the distal tip to a distal end of an insertion tube; and coupling a lumen passing through the insertion tube to supply a fluid to the distal tip so that the fluid exits from the distal tip through the perforations.

In a disclosed embodiment, creating the plurality of the perforations includes bringing a needle electrode into proximity with the outer surface of the distal tip at a location of each of the perforations, and applying an electrical potential so as to create an electrical discharge between the needle electrode and the outer surface, thereby perforating the outer surface.

The present invention will be more fully understood from the following detailed description of the embodiments thereof, taken together with the drawings in which:

DETAILED DESCRIPTION OF EMBODIMENTS

Figure 1:
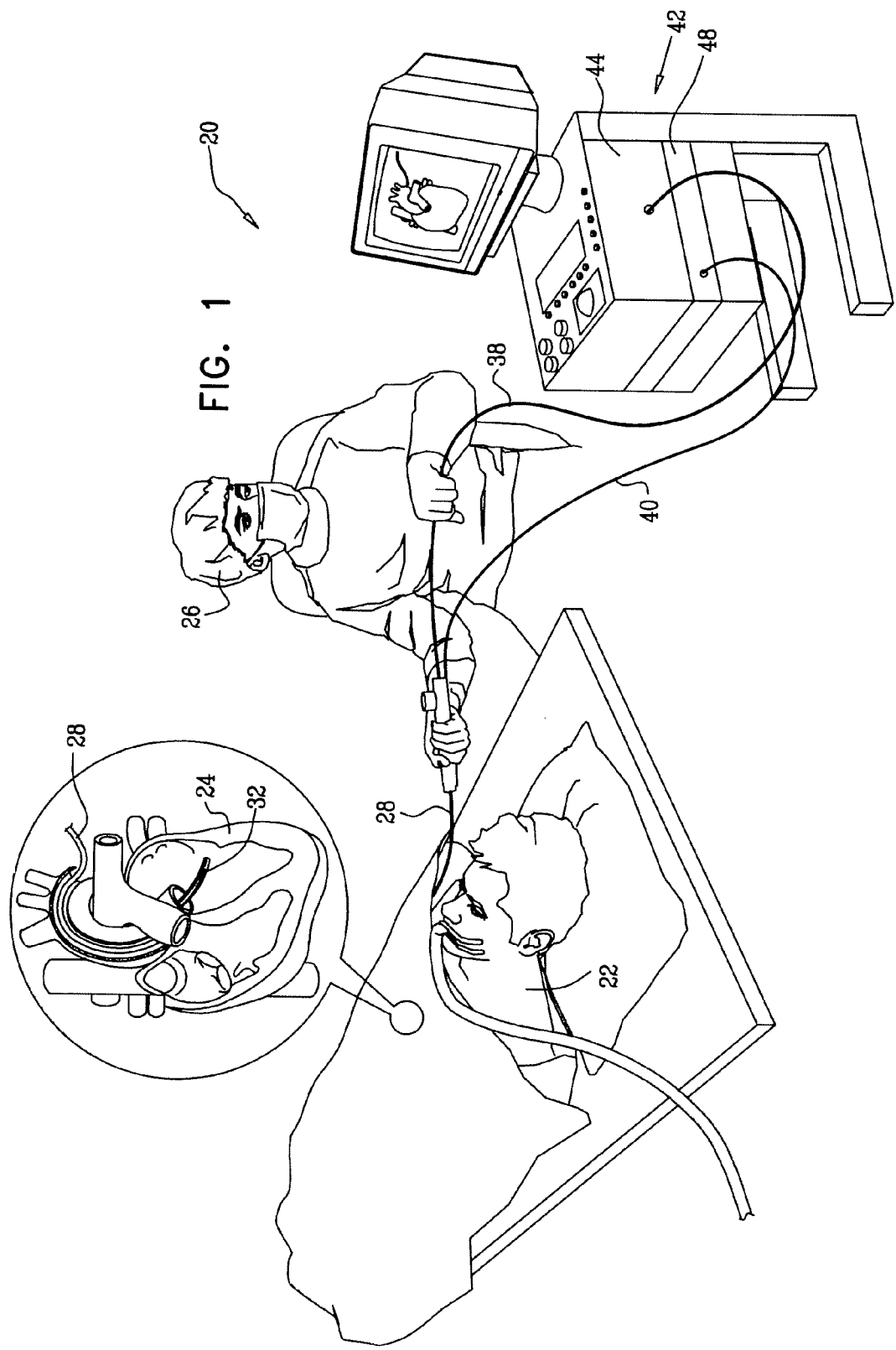
FIG. 1 is a schematic, pictorial illustration of a system for cardiac ablation therapy, in accordance with an embodiment of the present invention.

FIG. 1 is a schematic, pictorial illustration of a system 20 for cardiac ablation therapy, in accordance with an embodiment of the present invention. An operator 26 inserts a catheter 28 through a blood vessel into a chamber of a heart 24 of a subject 22, and manipulates the catheter so that a distal end 32 of the catheter contacts the endocardium in an area that is to be treated. The distal tip of the catheter is perforated to enable optimal irrigation of the treatment area, as shown and described hereinbelow. In other respects, however, system 20 resembles systems for cardiac ablation treatment that are known in the art, such as the above-mentioned Biosense Webster system, and the components of such systems may be adapted for use in system 20.

After positioning distal end 32 at an ablation site, and ensuring that the tip is in contact with the endocardium at the site, operator 26 actuates a radio frequency (RF) energy generator 44 in a control console 42 to supply RF energy via a cable 38 to distal end 32. Meanwhile, an irrigation pump 48 supplies a cooling fluid, such as saline solution, via a tube 40 and a lumen in catheter 28 to the distal end. Operation of the RF energy generator and the irrigation pump may be coordinated in order to give the appropriate volume of irrigation during ablation, so as to cool the tip of the catheter and the tissue without overloading the heart with irrigation fluid. A temperature sensor (not shown in the figures) in distal end 32 may provide feedback to console 42 for use in controlling the RF energy dosage and/or irrigation volume.

Figure 2:
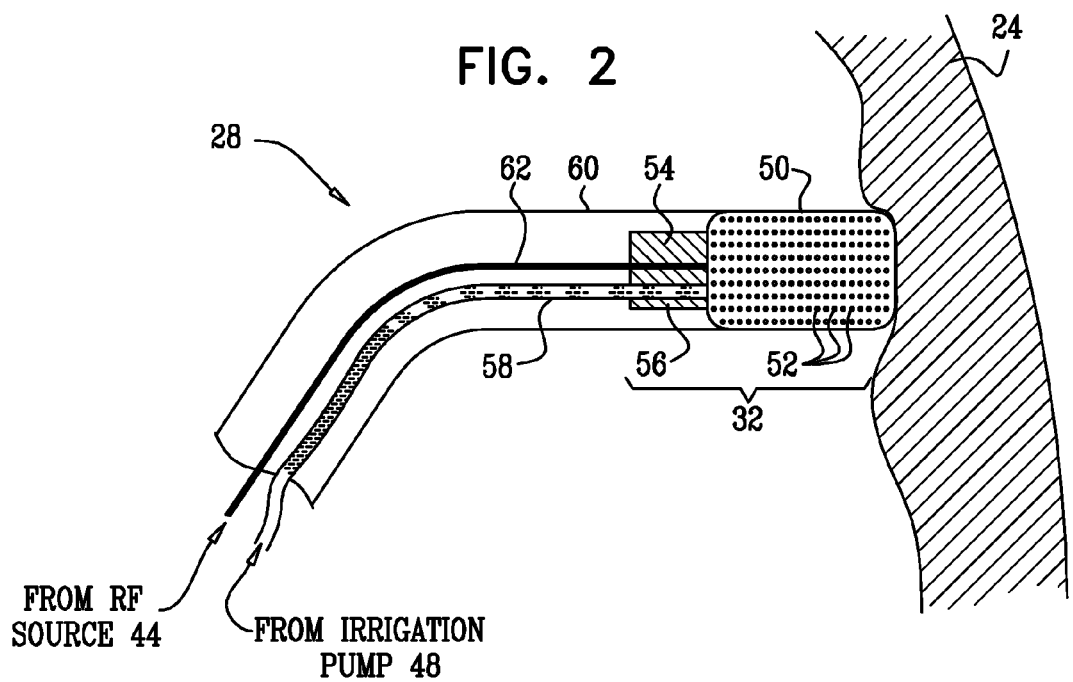
FIG. 2 is a schematic sectional view of the distal end of a catheter in engagement with heart tissue, in accordance with an embodiment of the present invention.

FIG. 2 is a schematic sectional view of distal end 32 of catheter 28 in engagement with endocardial tissue in heart 24, in accordance with an embodiment of the present invention. The catheter terminates in a distal tip 50, which is fixed to the distal end of an insertion tube 60 of the catheter. The distal tip typically comprises a conductive material, such as platinum, while the insertion tube has an insulating flexible outer sheath. The outer surface of the distal tip is penetrated by multiple perforations 52, which are distributed over the surface of the distal tip both longitudinally (i.e., along the direction parallel to the longitudinal axis of catheter 28) and circumferentially (along circumferences around the axis).

Figure 3:
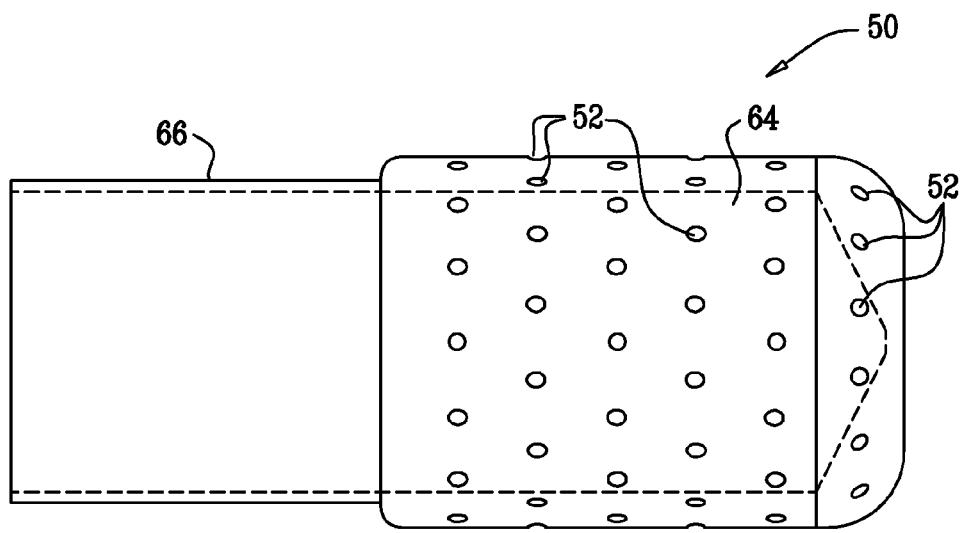
FIG. 3 is a schematic side view of the distal tip of a catheter, in accordance with an embodiment of the present invention.

FIG. 3 is a schematic side view of distal tip 50, showing details of perforations 52, in accordance with an embodiment of the present invention. The distal tip is hollow, with an outer surface 66 that encloses an interior space 64. Perforations 52 extend from the outer surface into the interior space. For cardiac ablation applications, the distal tip shown in FIG. 3 is typically about 2.5 mm in diameter and 6 mm long, with a wall thickness in the distal part of the tip of about 0.25 mm. These dimensions, however, are given solely by way of illustration, and larger or smaller dimensions may be used depending on application requirements. The edges of the distal tip, at both the distal and proximal extremities of the tip, are typically rounded in order to avoid possible concentration of the RF electric field around the edges.

Typically, distal tip 50 has at least eight perforations, which are less than 0.5 mm in diameter, in order to distribute the irrigation over the tip both longitudinally and circumferentially without overloading the heart with the cooling fluid. The inventors have found it advantageous, however, to have at least fifty perforations in the distal tip, with diameters no greater that 0.2 mm. In the actual embodiment that is shown in FIG. 3, tip 50 has ninety-six perforations, with diameters of approximately 0.1 mm. The sizes of the perforations may optionally be varied over the length of the distal tip to compensate for pressure variation and ensure equal flow over the entire length. For this purpose, the perforations at and near the most distal part of the tip may be made larger than the more proximal perforations, which are nearer to the fluid inlet.

Returning now to FIG. 2, the proximal end of distal tip 50 is closed off by a plug 54, which has a fluid inlet 56 feeding interior space 64. A lumen 58 passing through insertion tube 60 of catheter 28 conveys fluid from irrigation pump 48 (FIG. 1) to inlet 56, filling interior space 64. The fluid exits tip 50 through perforations 52 to the surrounding tissue. A conductor 62 conveys RF energy from RF generator 44 to the conductive tip, which thus serves as an electrode for delivering the energy in order to ablate the tissue.

Figure 4:
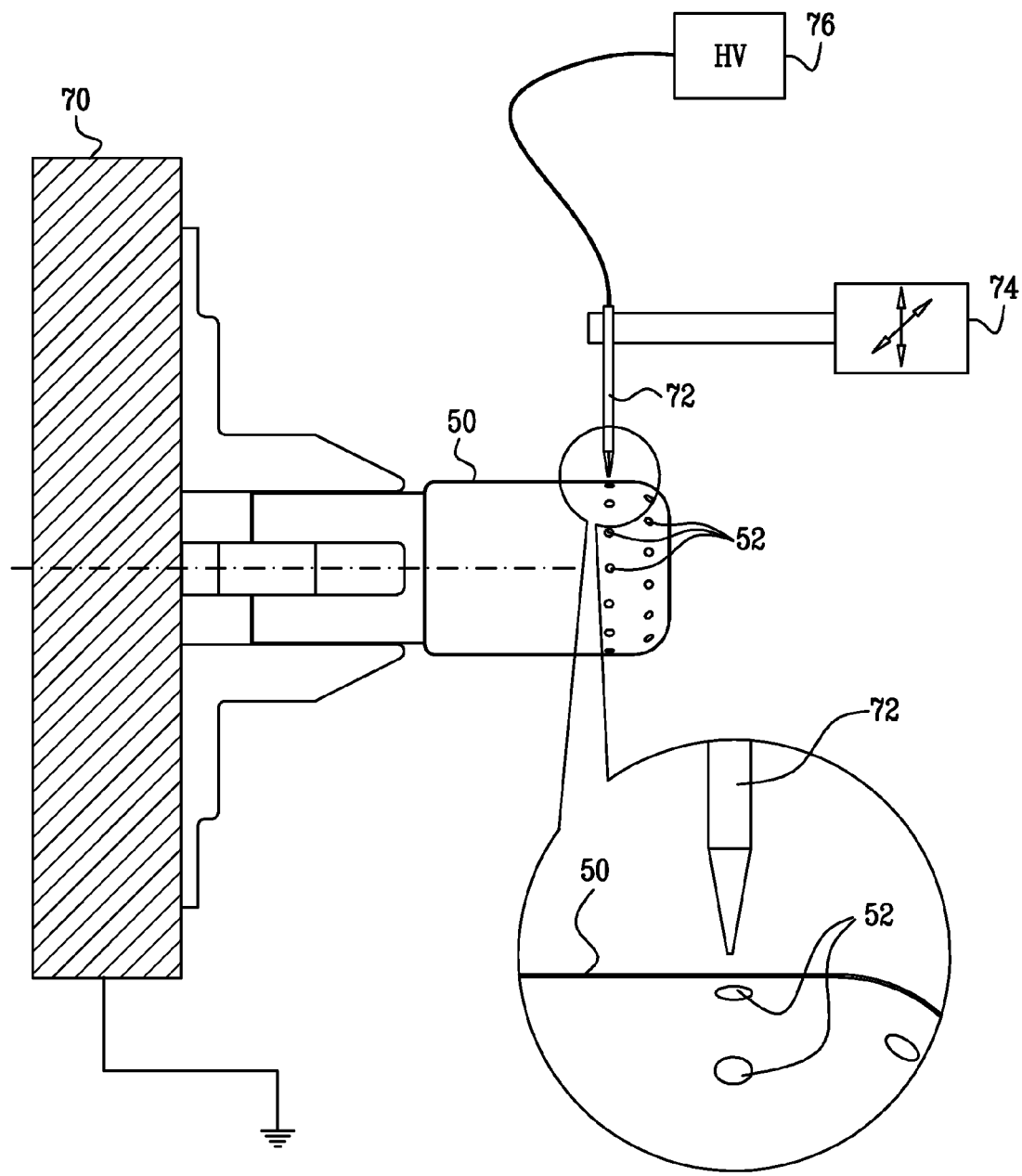
FIG. 4 is a schematic side view of apparatus used in producing a perforated catheter tip, in accordance with an embodiment of the present invention.

FIG. 4 is a schematic side view of apparatus used in creating perforations 52 in distal tip 50, in accordance with an embodiment of the present invention. In this embodiment, the perforations in the tip are produced by electrical spark discharge. Tip 50 is mounted in a suitable rotating jig 70 (such as a lathe chuck). A needle electrode 72, such as a carbon needle, is held at a potential of several thousand volts by a high-voltage power supply 76. A motion assembly 74 gradually brings the needle electrode into proximity with the point on the catheter tip at which a perforation is to be made. The procedure is typically carried out in a controlled gas environment (such as an argon atmosphere). At a distance of about 1 mm, a spark jumps from the electrode to the catheter tip. The discharge creates a small perforation, typically about 100 μm in diameter, in the tip. The size of the hole may be controlled by varying the discharge voltage.

Jig then rotates tip 50 so that the location of the next perforation is positioned opposite needle electrode 72, and the next perforation is created in similar fashion. The electrode is shifted longitudinally along the catheter tip to make multiple sets of holes, which are distributed longitudinally and circumferentially over the catheter tip as described above.

This method of creating holes in distal tip 50 permits a large number of holes to be made precisely and inexpensively, without structurally weakening the catheter tip. It allows the sizes of the irrigation holes to be controlled in production to give precisely the desired volume of irrigation, without clogging of the holes on the one hand or overloading of the heart with irrigation fluid on the other.

Although the embodiments described above relate specifically to catheters used in RF ablation treatment within the heart, the principles of the present invention may similarly be applied to other organs and in other types of therapy that involve application of energy to body tissues. For example, a device with a similar sort of irrigated tip may be used in therapies that involve microwave-based or ultrasonic tissue heating.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical device, comprising:
   an insertion tube, having a distal end for insertion into a body of a subject at a treatment area;
   a conductive hollow distal tip including a cylindrically shaped outer surface having a diameter and a circumference and defining a longitudinal axis and proximal and distal ends, and a planar end cap integrated along the distal end, the planar end cap having a planar section that extends across the diameter of the cylindrically shaped outer surface to enclose an interior space, the planar end cap is configured to be substantially perpendicular to the longitudinal axis, which conductive hollow distal tip is fixed to the distal end of the insertion tube and is coupled to a generator and is configured to directly apply energy to tissue at the treatment area inside the body, and wherein the conductive hollow distal tip has a distribution of perforations therethrough, and wherein there are at least 50 perforations in the distribution of perforations and at least a portion of the at least 50 perforations are circumferentially and longitudinally arranged over the cylindrically shaped outer surface of the hollow distal tip, wherein each perforation of the distribution of the at least 50 perforations is not greater than 0.2 mm in diameter; and
   a lumen passing through the insertion tube and coupled to deliver a cooling fluid to the tissue at the treatment area via the perforations, the distribution of the at least 50 perforations is configured to ensure equal flow of the cooling fluid while not overloading the treatment area with the cooling fluid;
   wherein the cylindrically shaped outer surface has edges along the circumference of the proximal and distal ends, wherein the edges are rounded and configured to avoid concentration of an electric field around the edges.

2. The device according to claim 1, wherein the distribution of the at least 50 perforations is a distribution of at least 96 perforations, each having a diameter less than or equal to approximately 0.1 mm.

3. The device according to claim 1, wherein the perforations in the distribution of perforations near the proximal end of the conductive hollow distal tip are smaller than the perforations in the distribution of perforations near the distal end of the conductive hollow distal tip to ensure equal flow over the length of the conductive hollow distal tip.

4. The device according to claim 3, wherein the wall thickness of the conductive hollow distal tip is approximately 0.25 mm.

5. The device according to claim 1, wherein the outer surface of the conductive hollow distal tip is configured to contact and apply electrical energy to the tissue so as to ablate the tissue.

6. The medical device of claim 1, further comprising a plug attached to the proximal end of the conductive hollow distal tip, the plug having a fluid inlet in communication with the interior space.

7. A medical apparatus, comprising:
   an elongate probe, for insertion into a body of a subject, the elongate probe comprising:
   an insertion tube, having a distal end for insertion into the body;
   a conductive hollow distal tip, which is fixed to the distal end of the insertion tube and is coupled to an energy generator to directly apply energy to tissue inside the body at a treatment area, and which has a cylindrically shaped outer surface having a diameter and a circumference, and defining a longitudinal axis and proximal and distal ends, and a planar end cap integrated along the distal end, the planar end cap having a planar section that extends across the diameter of the cylindrically shaped outer surface to enclose an interior space and has a distribution of at least 50 perforations distributed through the conductive hollow distal tip, and wherein at least a portion of the at least 50 perforations are circumferentially and longitudinally arranged over the cylindrically shaped outer surface of the conductive hollow distal tip, wherein each perforation of the distribution of the at least 50 perforations is not greater than 0.2 mm in diameter, and wherein the perforations in the distribution of the at least 50 perforations near the proximal end of the conductive hollow distal tip are smaller than the perforations in the distribution of the at least 50 perforations near the distal end of the conductive hollow distal tip and configured to ensure equal flow over the length of the conductive hollow distal tip;
   a lumen passing through the insertion tube and in fluid communication with the distribution of the at least 50 perforations;
   the energy generator, for coupling to the elongate probe so as to supply the energy to the conductive hollow distal tip; and
   an irrigation pump, for coupling to the lumen so as to supply the cooling fluid via the lumen and the distribution of the at least 50 perforations to the tissue;
   wherein the cylindrically shaped outer surface has edges along the circumference of the proximal and distal ends, wherein the edges are rounded and configured to avoid concentration of an electric field around the edges.

8. The apparatus according to claim 7, wherein the cylindrically shaped outer surface of the conductive hollow distal tip comprises a conductive material and is configured to contact the tissue, and wherein the energy generator is coupled to supply electrical energy to the conductive hollow distal tip in order to ablate the tissue.

9. The apparatus according to claim 8, wherein the elongate probe is configured for insertion through a blood vessel into a heart of the subject for ablation of myocardial tissue in the heart.

10. The medical apparatus according to claim 7, wherein the wall thickness of the conductive hollow distal tip is approximately 0.25 mm.

11. The medical device of claim 7 further comprising a plug attached to the proximal end of the conductive hollow distal tip, the plug having a fluid inlet in communication with the interior space.

12. A method for treatment, comprising:
   inserting an elongate probe into a body of a subject, the elongate probe comprising:
   an insertion tube, having a distal end for insertion into the body;

a conductive hollow distal tip, which is fixed to the distal end of the insertion tube and which has a cylindrically shaped outer surface having a diameter and a circumference and defining a longitudinal axis and proximal and distal ends and an end cap integrated with the cylindrical shaped outer surface to enclose an interior space, the end cap having a planar section lying in a plane substantially perpendicular to the longitudinal axis and extending across the diameter of the cylindrically shaped outer surface, wherein the cylindrically shaped outer surface has edges along the circumference of the proximal and distal ends, wherein the edges are rounded and configured to avoid concentration of an electric field around the edges, wherein such conductive hollow distal tip has a distribution of at least 50 perforations distributed through the cylindrical shaped outer surface, and wherein at least a portion of the distribution of the at least 50 perforations are circumferentially and longitudinally arranged over the cylindrically shaped outer surface of the conductive hollow distal tip, wherein each perforation in the distribution of the at least 50 perforations has a diameter not greater than 0.2 mm, the distribution of the at least 50 perforations being produced by electric spark discharge, and wherein the perforations in the distribution of the at least 50 perforations near the proximal end of the conductive hollow distal tip are smaller than the perforations in the distribution of the at least 50 perforations near the distal end of the conductive hollow distal tip and configured to ensure equal flow over the length of the conductive hollow distal tip; and a lumen passing through the insertion tube and in fluid communication with the at least 50 perforations;

applying energy through the conductive hollow distal tip to tissue inside the body; and supplying a cooling fluid via the lumen and the distribution of the at least 50 perforations to the tissue through equal flow of the cooling fluid to the tissue while not overloading the tissue with the cooling fluid.

13. The method according to claim 12, wherein inserting the elongate probe comprises inserting the elongate probe through a blood vessel into a heart of the subject, and wherein applying the energy comprises ablating myocardial tissue in the heart.

14. The method according to claim 12, wherein supplying the fluid comprises cooling the conductive hollow distal tip and the tissue.

15. The method according to claim 12, wherein the wall thickness of the conductive hollow distal tip is approximately 0.25 mm.

* * * * *